8/16/83 XR 4,398,539

United States Patent [19]

Proudian

[11] 4,398,539

[45] Aug. 16, 1983

[54] EXTENDED FOCUS TRANSDUCER SYSTEM

[75] Inventor: Andrew Proudian, Chatsworth, Calif.

[73] Assignee: Second Foundation, Rancho Cordova, Calif.

[21] Appl. No.: 164,830

[22] Filed: Jun. 30, 1980

[51] Int. Cl.[3] .......... A61B 10/00

[52] U.S. Cl. .......... 128/660; 73/626

[58] Field of Search .......... 128/660-661; 73/609, 618-626, 631, 642

[56] References Cited

U.S. PATENT DOCUMENTS

| | | | |
|---|---|---|---|
| 4,012,952 | 3/1977 | Dory | 73/626 |
| 4,137,777 | 2/1979 | Hoverl et al. | 128/660 X |
| 4,155,259 | 5/1979 | Engeler | 128/660 X |
| 4,161,121 | 7/1979 | Zitelli et al. | 128/660 X |
| 4,168,628 | 9/1979 | Vilkomeison | 128/660 X |
| 4,241,610 | 12/1980 | Anderson | 73/626 |
| 4,241,611 | 12/1980 | Specht et al. | 128/660 X |
| 4,276,491 | 6/1981 | Daniel | 128/660 X |
| 4,276,779 | 7/1981 | Davis, Jr. | 73/626 |

OTHER PUBLICATIONS

Ueda, M. et al., "Dynamic Focusing UTS Transducers Using Analog-Switch Phase Shifters", Electronics & Comm. in Japan, vol. 58, #12, 1975, p. 1.

*Primary Examiner*—Kyle L. Howell
*Assistant Examiner*—Francis J. Jaworski
*Attorney, Agent, or Firm*—Spensley, Horn, Jubas & Lubitz

[57] ABSTRACT

An ultrasound multi-electrode transducer together with electrical control means in which a central circular section and at least one annular peripheral section are successively electrically connected during transmit and receive functions so as to provide an increased focal zone.

14 Claims, 5 Drawing Figures

EXTENDED FOCUS TRANSDUCER SYSTEM

BACKGROUND OF THE INVENTION

1. Field of the Invention

The present invention relates to the field of ultrasonic scanners and in particular, to transducers used in medical diagnostic ultrasonic scanners.

2. Prior Art

Ultrasonic scanning instruments are used in medical diagnostics to view regions or particular organs within the body without the necessity of surgical incision to expose the area of interest. In its most fundamental operation, the ultrasonic scanning instrument is placed in contact with the surface of the body to be examined. The scanning instrument then emits a series of pulses, at an ultrasonic frequency, into the body being examined. During the time between the emission of the pulses, the instrument searches for and detects echoes of the emitted pulses which have been reflected by the various internal objects of interest. It is these echoes and their relationship to the emitted pulses which generates a representation or a "view" of the internal region or organs of interest.

A problem which has continued to plague the design and use of ultrasound transducers in medical diagnostic imaging relates to the compromise which must be made between the lateral resolution that can be achieved by such transducers and the range over which good lateral resolution can be maintained.

One prior art attempt to improve the lateral resolution of such transducers was to focus such transducers generally by curving the transducer crystal. For a circular transducer of diameter D operating at a wavelength $\lambda$, the transducer can be focused out to a focal distance F such that $F<D^2/4\lambda$. The lateral (Rayleigh) resolution achieved at the focus will then be $\rho_F \cong 1.22(F\lambda/D)$. The depth of focus of a transducer, i.e., the length of the region over which the resolution $\rho$ remains within some set factor of $\rho_F$ is $\Delta=k(F/D^2)\lambda$ (k=7 for the so-called '6 db down' criterion).

It can be seen from the equations for $\rho_F$ and $\Delta$ that, for a given wavelength $\lambda$, decreasing F/D (e.g., by increasing the size of the transducer) will decrease $\rho_F$ which is desirable, but will also decrease the depth of focus $\Delta$, which is undesirable. Similarly, increased depth of focus $\Delta$ is obtained at the expense of an increase in $\rho_F$.

Another prior art attempt which addressed this compromise between resolution and the depth of acceptable resolution was the replacement of a circular transducer of diameter D with a very narrow (typically one wavelength wide) annulus transducer of equal radius D. The resolution of such an annulus at any distance x beyond the first few diameters from its face is equal to $K(x\lambda/D)$; that is, such an annulus is essentially focused at all depths except near the transducer. The annulus suffers from several serious drawbacks, however, among them being that it has a poor beam pattern close to the transducer, large side lobes in its beam pattern and poor sensitivity because of its reduced area.

The limitations of an annular transducer can be minimized somewhat by use of a coaxial transducer wherein the central inner disk of the transducer is used as the transmitter and an annulus used as the receiver. See, for example the article by Reginald C. Eggleton entitled "Single Transducer Ultrasound Imaging", appearing in *Medical Physics,* Volume 3, No. 5, p. 303 (1976). The overall pattern of this transducer is the product of the transmit and receive patterns; thus, the inner disk will have the usual limited focal depth pattern, but will have minimal sidelobes, while the annular array will exhibit good resolution throughout the depth. This combination thus results in reduction (but not elimination) of the sidelobes at the expense of some loss of focal depth (compared to the annulus alone). However, it still does not resolve the problem of poor resolution within the first few diameters from the transducer face, and more seriously, the receiver sensitivity remains quite poor, because of the greatly reduced rceeiver area (typically a tenth to a twentieth of the full aperture).

Another approach which has been implemented to achieve high resolution over an acceptable range is by the use of phased annular arrays. In such arrays the single transducer crystal is replaced by a set of independently energized transducer elements in the shape of annuli. Typically ten elements are utilized, each connected to suitable transmit/receive electronics by means of variable delay lines. By this arrangement, the transmitted beam focus can be set at a selected value by appropriate delay in the transmit mode, while in the receive mode, the transducer can be dynamically focused by quasi-continuous variation of the interelement delays so as to 'track' the transmitted pulse as it travels into the object to be examined.

However, phased annular arrays also suffer from significant limitations. These limitationss include: cost and complexity; poor signal to noise characteristics; limited dynamic range; and relatively large sidelobes. Thus, the prior art attempts to achieve high resolution over an extended ranges have met with only limited success.

Accordingly, it is a general object of the present invention to provide an improved ultrasonic transducer system.

It is a further object of the present invention to provide a simple means of extending the focal depth of a transducer while providing improved focusing characteristics over existing devices.

SUMMARY OF THE INVENTION

A transducer system for use in ultrasonic scanning devices is provided. The system includes a transducer adapted to emit ultrasonic waves in response to a signal from a transmitter, to detect echoes of the ultrasonic waves it has emitted, and to provide information to additional processing means which is indicative of the echoes which the transducer has detected. The transducer is typically comprised of a piezoelectric crystal which has been formed into a semi-spherical shape and which has electrodes attached to both surfaces thereof. On a first surface of the crystal there is located a central section which is surrounded by at least one peripheral section. The peripheral sections are electrically isolated from the central section and from one another. The transducer system further comprises a means for selectively electrically coupling the central section and the peripheral sections on the transducer to the transmitter and the processing means in at least two configurations. For each of these various configurations, the transducer is caused to emit ultrasonic waves which converge at different points, a pre-selected distance beyond the transducer. In addition, for each of the configurations, ultrasonic echoes which emanate from different ranges of distances of interest beyond the transducer are substantially in focus at the transducer.

The novel features which are believed to be characteristic of the invention, both as to its organization and its method of operation, together with further objects and advantages thereof, will be better understood from the following description in connection with accompanying drawings in which presently preferred embodiments of the invention are illustrated by way of example. It is to be expressly understood, however, that the drawings are for purposes of illustration and description and are not intended as a definition of the limits of the invention.

DETAILED DESCRIPTION OF THE INVENTION

Figure 1:
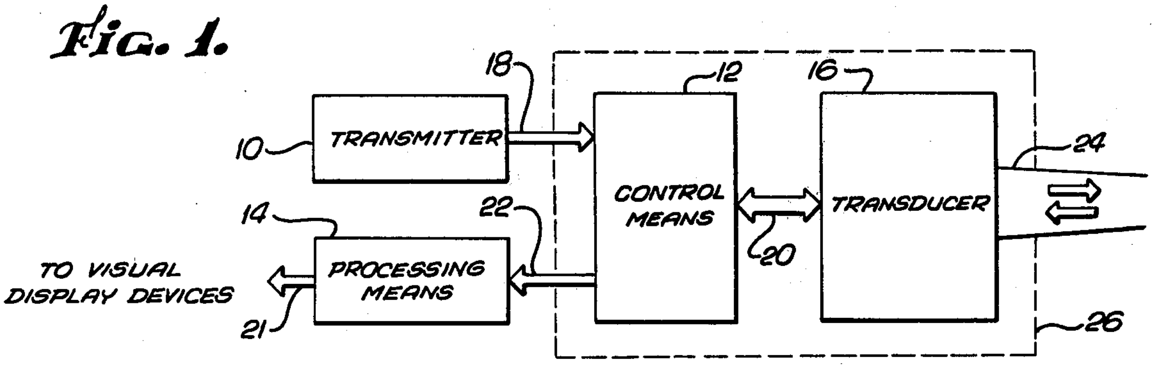
FIG. 1 is a block diagram of the transducer system of the present invention.

Referring to FIG. 1, a block diagram of the transducer system 26 of the present invention is illustrated. Transducer system 26 is comprised of the transducer 16 coupled to a control means 12 via a plurality of lines 20. As will be described more fully hereinbelow, transducer 16 is comprised of a semi-spherical crystal element which has readily selectible active areas. When configured and operated as disclosed herein, transducer system 26 will emit ultrasonic waves 24 which can be controlled so as to converge at two or more different points a pre-selected distance beyond transducer 16. Furthermore, transducer 16 is adapted such that echoes resulting from ultrasonic waves produced by transducer 16 are substantially in focus at transducer 16 substantially throughout the range of distances of interest for each of the points of convergence.

Coupled to control means 12 are the transmitter 10 and processing means 14, the interconnection being made via the plurality of lines 18 and 22 respectively. Transmitter 10 can be one of many numerous devices for providing the appropriate drive signal to a transducer so as to cause that transducer to emit pulses of ultrasonic frequency at a suitable repetition rate. Such pulse generators are well known in the art and will not be discussed further herein. Similarly, processing means 14 can include such conventional devices as scan convertors, display deflection circuits and a variety of other well-known devices adapted to produce an output signal which is indicative of the image resulting from the echoes being returned to transducer 16. Typically, processing means 14 would be coupled, via lines 21 and a variety of other conventional devices, to a video display. In response to the signals produced by processing means 14, the video display will display a visual image of a region of the human patient being scanned by the transducer system 26.

Figure 2:
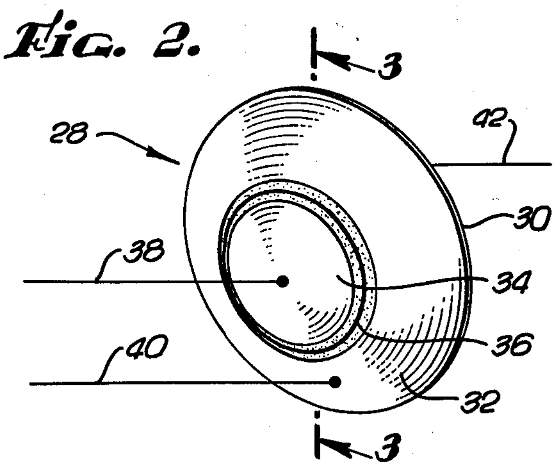
FIG. 2 is a perspective view of the transducer crystal of the present invention.

Now referring to FIG. 2, the transducer crystal 28 of transducer 16 is illustrated in a perspective view. Transducer crystal 28 is comprised of a conventional piezoelectric material 30 to which has been attached metalized electrodes on both of the larger surfaces thereof. Transducer crystals 28 can be made of lead zirconate titanate or similar piezoelectric material. As will be discussed more fully hereinbelow, transducer 16 is also comprised of a backing material (not shown) adjacent the electrodes.

On one surface of crystal 28 are disposed a central section electrode 34 surrounded by at least one peripheral section electrode 32. Peripheral electrode 34 is electrically isolated from the central electrode 34 by means of the guard ring 36. On the opposite side of transducer crystal 28 is one ground electrode (not illustrated) which substantially covers that surface of the crystal 28. Electrical line 38 is directly coupled to central section electrode 34, while peripheral section electrode 32 is electrically coupled via line 40. In addition, the ground electrode on the reverse side of crystal 30 is electrically connected via line 42.

The guard ring electrode 36 is not strictly necessary but serves to isolate the two electrodes 32 and 34, and thus reduce cross talk. Another means of reducing cross talk is to saw through the transducer crystal 30, thus creating two physically separated parts, namely, the central section 34 and the peripheral section 32. However, this physical separation is somewhat more difficult to fabricate especially if a three or more piece configuration or noncircular transducer geometries are used. In addition, physical separation can lead to unwanted vibration modes of the transducer crystal 28.

As shown in FIG. 2, electrodes 32 and 34 are disposed on transducer crystal 28 in such a manner that electrical activation of each electrode results in a corresponding and limited activation of the crystal 30. That is, because each electrode 32, 34 is physically limited to a certain area on the surface of crystal 30, electrical excitation of one of those electrodes (in conjunction with the grounded electrode) results in the piezoelectric effect being generally limited to that same area of the crystal 30. Thus, transducer crystal 28 is effectively divided into a center transducer section 33 and a peripheral (or annular) transducer section 31, each section corresponding to electrodes 34 and 32 respectively.

Figure 3:
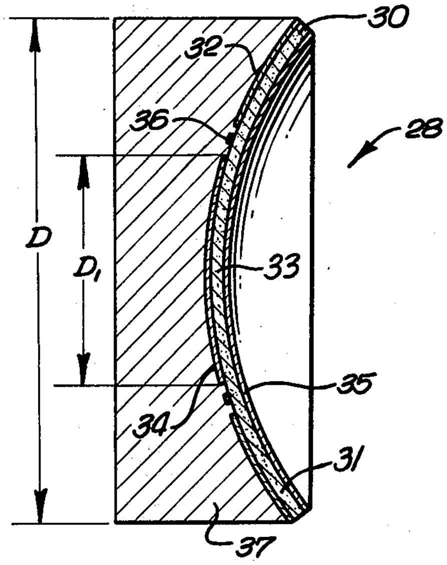
FIG. 3 is a cross-sectional view of the transducer crystal of the present invention.

FIG. 3 is a cross-sectional view of transducer crystal 28 which illustrates the relationship between central section electrode 34, the peripheral electrode 32, and the ground electrode 35 on the opposite surface of crystal 28. Central section electrode 34 is disposed in the center portion of the crystal 28 and has a diameter of length $D_1$. Disposed around the outer surface of crystal 28 is the peripheral electrode 32, electrode 32 being electrically isolated from central section electrode 34 by the guard ring 36. On the surface of crystal 28, which is opposite central section electrode 34 and peripheral electrode 32, is ground electrode 35.

As can be seen in FIG. 3, ground electrode 35 substantially covers the inner surface of transducer crystal 28, while backing material 37 substantially covers the outer surface of crystal 28. Backing material 37 can be any well known material which can readily absorb accoustical energy. Finally, FIG. 3 illustrates that the total diameter of crystal 30 is of a length D.

Figure 4:
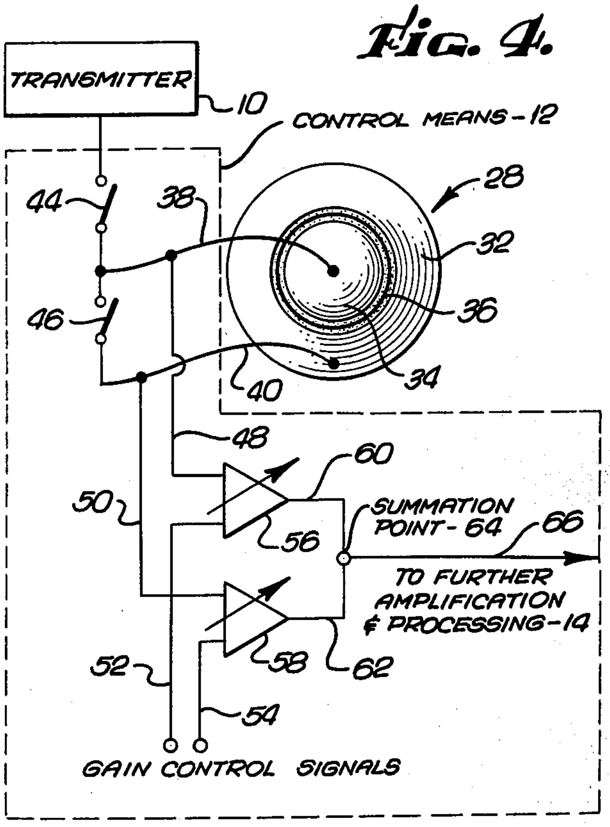
FIG. 4 is a schematic diagram of one embodiment of the transducer system of the present invention.

Now referring to FIG. 4, a schematic diagram of one embodiment of the present invention is illustrated. Generally, transmitter 10 is coupled to control means 12, while control means 12 is coupled to transducer crystal 28. More specifically, transmitter 10 is coupled to central section electrode 34 and annular section electrode 32 by means of lines 38 and 40 respectively, and time-controlled switches 44 and 46 respectively. Central section 34 is also coupled to gain controlled amplifier 56 via line 48. Similarly, annular electrode 32 is coupled to gain controlled amplifier 58 via line 50. The output of amplifier 56 is coupled to the summation point 64 by means of line 60, while the output of amplifier 58 is coupled to the summation point 64 by line 62. The output of summation point 64 is coupled to processing means 14 via output line 66.

In operation, the transmitter 10 is connected by time-controlled switches 44 and 46 to either or both electrodes 32, 34. The selection of electrodes 32, 34 depends upon whether it is desired that the transmitted beam pattern correspond to the small aperture $D_1$ or the full aperture D. The selection can be made by the operator of the ultrasonic scanning device, depending on the specific area of interest to be viewed. After the transmitter 10 has been activated, so that transducer crystal 28 emits an ultrasonic pulse, switches 44 and 46 are opened and, initially, the central electrode 34 is used to receive the ultasonic echoes. This selective utilization of central electrode 34 is accomplished by setting the gain of variable gain amplifier 56 to "G", by means of line 52, and the gain of amplifier 58 to "0" by means of line 54. In this manner peripheral electrode 32 is effectively decoupled from the output line 66.

After a time period $T_1$, corresponding to the time required for reflected echoes to arrive at the transducer 28 from a distance $X_1$ in the body, the gain of amplifier 56 is smoothly but rapidly (typically in a few to perhaps 10 microseconds) reduced from G to G/a while the gain of amplifier 58 is simultaneously increased from 0 to G/b. (Typically a=b=2) Thus, both central electrode 34 and peripheral electrode 32 are coupled to the output line 66.

Figure 5:
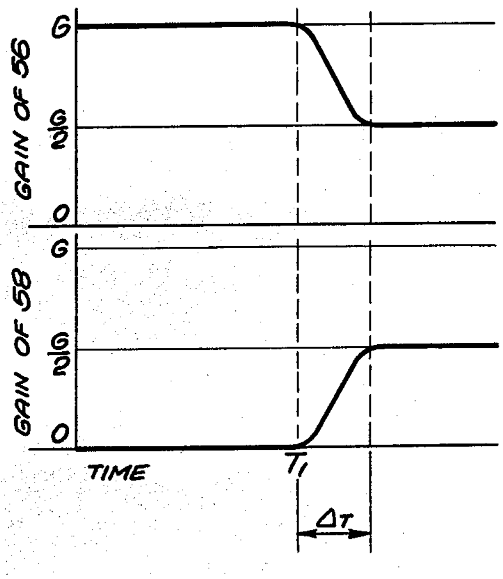
FIG. 5 is a timing diagram of the amplifier gain versus time as used in one embodiment of the present invention.

New referring to FIG. 5, the gain of amplifiers 56 and 58 is displayed as a function of time the case a=b=2. As described hereinabove, the central transducer 33 is initially used to receive. This selective coupling of the transducer sections 33, 35 to the processing means 14 is accomplished by varying the gain of the gain controlled amplifiers 56 and 58. Thus, because the annular transducer section 33 is not to be initially coupled to the processing means 14, the gain of amplifier 58 (which couples annular section 33 to processing means 14) is set at 0 during the initial time. Then, after the elapse of time period $T_1$, the gain of amplifier 58 is smoothly increased to G/2, while the gain of amplifier 56 is decreased to G/2. Thus, after the elapse of the time period $\Delta T$, the gain of both amplifiers 56 and 58 are set at G/2 so that both the central transducer section 35 and the annular transducer section 33 are coupled to the processing means 14.

The principle of operation of the present invention is based on several facts and observations. First, it is known that a transducer crystal of radius of curvature R will be focused at a distance $F \approx R$ provided that its diameter is sufficiently large, (i.e., when $D^2/4\lambda > R$). Furthermore, such a transducer crystal will be focused at a distance F somewhat short of $D^2/4\lambda$ when $R \geqq D^2/4\lambda$. What has been observed is that for a crystal of a given curvature R, the acoustic beam pattern retains a well-focused structure down to values of aperture diameter D such that $D^2/4\lambda \cong R/3$. Thus, if the diameter of a transducer of curvature R is progressively reduced, its focal length will vary from $F \simeq R$ down to a value F as low as R/3 with almost the same beam pattern as if its curvature radius were also being reduced.

The present invention utilizes the relationship illustrated above to make a given transducer crystal of radius R act like two or more transducers of focal lengths $F_1, F_2, \ldots, F$ by varying the effective diameter of the crystal to values $D_1, D_2, \ldots D$. The values $F_i$, and $D_i$ are selected so as to have overlapping zones of focus and thereby achieve an extended focal zone.

For ease in description, the theory of operation of the two element case, as illustrated in FIG. 2, will be described in more detail: The live electrode of the transducer is configured as a central section 34 of diameter $D_1$ separated from an annular section 32 by a guard ring 36. The guard ring 36 is electrically grounded, and is quite narrow (typically, the guard ring and unelectroded spaces would add up to a total width of 10 mils). The ground electrode, on the other face of crystal 28 (not shown) is monolithic.

Typical parameters for the two-element case would be as follows: For a typical case of pulse frequency of 3 MHz ($\lambda \simeq 0.05$ cm), D=1.8 cm, $R \simeq F = 14$ cm ($D^2 \cong 16$ cm R) and $D_1 = 1.0$ cm so that $F_1 \simeq (D_1^2/4\lambda) \simeq 5$ cm.

For the typical parameters cited above, the inner diameter element (i.e., that portion of the transducer which is made active by central section 34) will be focused over a focal zone $F_1 \pm (\Delta_1/2)$ so that since $$\Delta_1 \simeq \frac{7}{16} \frac{D_1^2}{\lambda} \simeq 9 \text{ cm},$$

the inner element will be focused from less than 1 cm to over 9 cm. The focal zone of the combination of the central electrode 34 and the outer ring 32, (i.e., the full aperture of diameter D) will extend over a zone $F \pm (\Delta_2/2)$. Because $$\Delta \cong \frac{7F^2\lambda}{D^2} \cong 15 \text{ cm},$$

the focused region for the combination will be from about 7 cm to over 20 cm. In this example, the cross-over region would begin around $X_1 \cong 8$ cm (e.g., from 8 cm to 9 cm).

Of course, alternate embodiments of the present invention are readily apparent to those skilled in the art. One embodiment (not illustrated) would simply be to transmit and receive by means of one of the two sections of the transducer 28. That is, the transducer system 26 could be readily configured such that there are two functions of operation. The first function would be to transmit by means of the central section 35 and correspondingly, receive by means of that same section. The second function would be to transmit by means of the combination of central section 35 and annular section 33, and then to receive by that same combination. Thus, a single transducer could be operated either as a short focal depth or a long focal depth transducer.

A further embodiment would be to use a three (or more) electrode configuration. In this embodiment additional peripheral electrodes would be disposed about peripheral electrode 32, while the diameter of electrode 32 would be reduced correspondingly. The advantage of these additional electrodes would be the ability to "fine tune" the three (or more) overlapping focal zones, and the transmit beam could be focused at three (or more) rather than two selected points. However, the simplicity of the arrangement quickly becomes lost, and two electrodes are enough for most cases of interest in medical diagnostics.

It can be seen from the above description that there are important differences between the present invention and the prior art wherein a central disk is used to transmit and a very thin annulus is used to receive. One difference is that the present invention always uses a full electrode to receive (either $D_1$ or the full disk D), and thus achieves much higher sensitivity. Furthermore, the relatively small loss of sensitivity due to use of a smaller electrode 34 in the present invention occurs in the near part of the field where there has been relatively little attenuation due to intervening tissue, so that echoes are still strong. Typically, the receive sensitivity of the present invention is ten to twenty times higher than that of the prior art. In addition, the present invention has no sidelobe problems, and no "near focus" problems. Compared to a phased annular array, the present invention not only can use far fewer elements (two generally suffice), but there are no variable delay lines, so that all the switching problems, limited dynamic range problems, and numerous other problems of phased arrays are eliminated.

While specific embodiments of the present invention have been disclosed and described in detail herein, it will be understood by those skilled in the art that various changes in form and detail may be made therein without departing from the spirit and scope of the invention. For example, the number, specific shape and specific configuration of the electrodes on the transducer crystal can be varied without departing from the scope of the present invention.

I claim:

1. A transducer system for use in ultrasonic scanning devices comprising:

(i) A piezoelectric transducer of a dish configuration having a spherical surface and a radius of curvature R and adapted to emit ultrasonic waves having a wavelength $\lambda$ in response to a signal from a transmitter, detect echoes of said ultrasonic waves, and provide information to a processing means which is indicative of said detected echoes, said transducer including a central circular section of diameter $d_1$, where $d_1$ is approximately equal to $2\sqrt{\lambda R/3}$ and an annular peripheral section surrounding said central section, said peripheral and central sections having a combined diameter of $d_2$, where $d_2$ is approximately equal to $2\sqrt{\lambda R}$, said peripheral section being electrically isolated from said central section; and (ii) control means for selectively electrically coupling said central section alone and in combination with said peripheral section to said transmitter to form two operational configurations of the transducer during a transmission mode, whereby said transducer emits ultrasonic waves which, for each of said configurations, converge at a different focal point approximately within the range R/4 to R beyond said transducer, said control means also for selectively electrically coupling said central section alone and in combination with said peripheral section to said processing means to form two operational configurations of the transducer during a reception mode, whereby for each of said configurations ultrasonic echoes which emanate from different distances of interest beyond said transducer, within overlapping zones of focus for each focal point, are substantially in focus at said transducer.

2. The transducer system of claim 1 wherein said piezoelectric transducer includes a piezoelectric portion and said central section includes a generally circular electrode disposed on said piezoelectric portion and said peripheral section includes a generally annular electrode disposed on said piezoelectric portion so as to surround said central section, said transducer further including a common electrode disposed on said piezoelectric portion opposite said central circular and annular electrode sections.

3. The transducer system of claim 1 wherein said central section and said peripheral section are physically separated from one another thereby causing a mechanical isolation of said central section and said peripheral section from one another.

4. The transducer system of claim 3 wherein said control means comprises gain-controlled switches, whereby said peripheral section is coupled to said processing means along with said central section by smoothly decreasing the gain of the switch which couples the central section to said processing means while smoothly increasing the gain of the switch which couples said peripheral section to said processing means.

5. A transducer system for use in ultrasonic scanning devices comprising:

(i) a piezoelectric transducer of a dish configuration having a spherical surface and a radius of curvature R and adapted to emit ultrasonic waves having a wavelength $\lambda$ in response to a signal from a transmitter, detect echoes of said ultrasonic waves, and provide information to a processing means which is indicative of said detected echoes, said transducer including a central circular section of diameter $d_1$, where $d_1$ is greater than $2\sqrt{\lambda R/3}$, but less than $2\sqrt{\lambda R}$, and an annular peripheral section surrounding said central section, said peripheral and central sections having a combined diameter of $d_2$, where $d_2$ is greater than $2\sqrt{\lambda R}$, said peripheral section being electrically isolated from said central section; and (ii) control means for selectively electrically coupling said central section alone and in combination with said peripheral section to said transmitter to form two operational configuration of the transducer during a transmission mode, whereby said transducer emits ultrasonic waves which converge at a different focal point approximately within the range $d_1^2/4$ to R beyond said transducer for each of said configurations, said control means also for selectively electrically coupling said central section alone and in combination with said peripheral section to said processing means to form two operational configurations of the transducer during a reception mode, whereby for each of said configurations ultrasonic echoes which emanate from different distances of interest beyond said transducer, within overlapping zones of focus for each focal point, are substantially in focus in said transducer.

6. The transducer system of claim 5 wherein said piezoelectric transducer includes a piezoelectric portion and said central section includes a generally circular electrode disposed on said piezoelectric portion and said peripheral section includes a generally annular electrode disposed on said piezeoelectric portion so as to surround said central section, said transducer further including a common electrode disposed on said piezoelectric porton opposite said central circular and annular electrode sections.

7. The transducer system of claim 6 wherein said central section and said peripheral section are physically separated from one another thereby causing a mechanical isolation of said central section and said peripheral section from one another.

8. The transducer system of claim 7 wherein said control means comprises gain-controlled switches, whereby said peripheral section is coupled to said processing means along with said control section by smoothly decreasing the gain of the switch which couples the central section to said processing means while smoothly increasing the gain of the switch which couples said peripheral section to said processing means.

9. A transducer system for use in ultrasonic scanning devices comprising:

(i) a piezoelectric transducer of a dish configuration having a spherical surface and a radius of curvature R and adapted to emit ultrasonic waves having a wavelength λ in response to a signal from a transmitter, detect echoes of said ultrasonic waves, and provide information to a processing means which is indicative of said detected echoes, said transducer including a central circular section of diameter $d_1$, where $d_1$ is approximately equal to $\overline{2\sqrt{\lambda R/3}}$, and an annular peripheral section surrounding said central section, said peripheral and central sections having a combined diameter of $d_2$, where $d_2$ is approximately equal to $\overline{2\sqrt{\lambda R}}$, said peripheral section being electrically isolated from said central section; and (ii) control means for selectively electrically coupling said central section alone and in combination with said peripheral section to said transmitter during a transmission mode of operation and to said processing means during a reception mode of operation, including at least two operator-selectable functions whereby in a first function said control means initially couples said central section to said transmitter, then decouples said central section from said transmitter and couples said central section to said processing means, and then, after the elapse of a predetermined time period, further couples said peripheral section to said processing means, thereby substantially focusing at said transducer echoes returning from different distances of interest beyond said transducer, within overlapping zones of focus, and whereby in a second function said control means initially couples said peripheral section and said central section to said transmitter, then decouples said central section and said peripheral section from said transmitter and couples said central section to said processing means, and then, after the elapse of a predetermined time period, further couples said peripheral section to said processing means thereby substantially focusing at said transducer echoes returning from different distances of interest beyond said transducer within overlapping zones of focus.

10. The transducer system of claim 9 wherein said piezoelectric transducer includes a piezoelectric portion and said central section includes a generally circular electrode disposed on said piezoelectric portion and said peripheral section includes a generally annular electrode disposed on said piezoelectric portion so as to surround said central section, said transducer further including a common electrode disposed on said piezoelectric portion opposite said central circular and annular electrode sections.

11. The transducer system of claim 10 wherein said central section and said peripheral section are physically separated from one another thereby causing a mechanical isolation of said central section and said peripheral section from one another.

12. The transducer system of claim 11 wherein said control means comprises gain-controlled switches, whereby said peripheral section is coupled to said processing means along with said central section by smoothly decreasing the gain of the switch which couples the central section to said processing means while smoothly increasing the gain of the switch which couples said peripheral section to said processing means.

13. A transducer system for use in ultrasonic scanning devices comprising:

(i) a piezoelectric transducer of a dish configuration having a spherical surface and a radius of curvature R and adapted to emit ultrasonic waves having a wavelength λ in response to a signal from a transmitter, detect echoes of said ultrasonic waves, and provide information to a processing means which is indicative of said detected echoes, said transducer including a central circular section of diameter $d_1$, where $d_1$ is approximately equal to $\overline{2\sqrt{\lambda R/3}}$ and a plurality of annular peripheral sections surrounding said central section, said peripheral and central sections having a combined diameter of $d_2$, where $d_2$ is approximately equal to $\overline{2\sqrt{\lambda R}}$, said peripheral sections being electrically isolated from said central section and from one another; and (ii) control means for selectively electrically coupling said central section and said peripheral sections to said transmitter when in a transmission mode and to said processing means when in a reception mode in a plurality of configurations, wherein in each configuration the electrical coupling forms a disc shaped transducer including the central section and one or more peripheral sections, whereby during the transmission mode said transducer emits ultrasonic waves which, for each of said configurations, converge at a different focal point approximately within the range R/3 to R beyond said transducer, and whereby during the reception mode for each of said configurations ultrasonic echoes which emanate from different distances of interest beyond said transducer, within overlapping zones of focus for each focal point, are substantially in focus at said transducer.

14. A transducer system for use in ultrasonic scanning devices comprising:

(i) a piezoelectric transducer of a dish configuration having a spherical surface and a radius of curvature R and adapted to emit ultrasonic waves having a wavelength λ in response to a signal from a transmitter, detect echoes of said ultrasonic waves, and provide information to a processing means which is indicative of said detected echoes, said transducer including a central circular section of diameter $d_1$, where $d_1$ is greater than $\overline{2\sqrt{\lambda R/3}}$ but less than $\overline{2\sqrt{\lambda R}}$, and a plurality of annular peripheral sections surrounding said central section, said peripheral and central sections having a combined diameter of $d_2$, where $d_2$ is greater than $\overline{2\sqrt{\lambda R}}$, said peripheral sections being electrically isolated from said central section and from one another; and (ii) control means for selectively electrically coupling said central section and said peripheral sections to said transitters when in a transmission mode and to said processing means when in a reception mode in a plurality of configurations, wherein in each configuration the electrical coupling forms a disc shaped transducer including the central section and one or more peripheral sections, whereby during the transmission mode said transducer emits ultrasonic waves which, for each of said configurations, converge at a different focal point approximately within the range $d_1^2/4$ to R beyond said transducer, and whereby during the reception mode for each of said configurations ultrasonic echoes which emanate from different distances of interest beyond said transducer, within overlapping zones of focus for each focal point, are substantially in focus in said transducer.

* * * * *